United States Patent
Wang et al.

(10) Patent No.: US 9,722,192 B2
(45) Date of Patent: Aug. 1, 2017

(54) METAL COMPLEX, PREPARATION METHOD AND USE THEREOF, AND DISPLAY DEVICE

(71) Applicants: BOE TECHNOLOGY GROUP CO., LTD., Beijing (CN); HEFEI BOE OPTOELECTRONICS TECHNOLOGY CO., LTD., Hefei, Anhui (CN)

(72) Inventors: Chengcheng Wang, Beijing (CN); Tianzhen Liu, Beijing (CN)

(73) Assignees: BOE TECHNOLOGY GROUP CO., LTD., Beijing (CN); HEFEI BOE OPTOELECTRONICS TECHNOLOGY CO., LTD., Hefei, Anhui (CN)

( * ) Notice: Subject to any disclaimer, the term of this patent is extended or adjusted under 35 U.S.C. 154(b) by 0 days.

(21) Appl. No.: 14/907,408

(22) PCT Filed: Jul. 14, 2015

(86) PCT No.: PCT/CN2015/083929
§ 371 (c)(1),
(2) Date: Jan. 25, 2016

(87) PCT Pub. No.: WO2016/138710
PCT Pub. Date: Sep. 9, 2016

(65) Prior Publication Data
US 2016/0380215 A1 Dec. 29, 2016

(30) Foreign Application Priority Data
Mar. 3, 2015 (CN) .......................... 2015 1 0095127

(51) Int. Cl.
| | |
|---|---|
| *C07F 15/00* | (2006.01) |
| *H01L 51/50* | (2006.01) |
| *H01L 51/00* | (2006.01) |
| *C07F 1/08* | (2006.01) |
| *C09K 11/06* | (2006.01) |
| *H05B 33/14* | (2006.01) |

(52) U.S. Cl.
CPC ............ *H01L 51/0085* (2013.01); *C07F 1/08* (2013.01); *C07F 15/00* (2013.01); *C07F 15/0033* (2013.01); *C09K 11/06* (2013.01); *H05B 33/14* (2013.01); *C09K 2211/1007* (2013.01); *C09K 2211/1014* (2013.01); *C09K 2211/1029* (2013.01); *C09K 2211/185* (2013.01); *H01L 51/5012* (2013.01)

(58) Field of Classification Search
CPC ................................ C07F 15/00; H01L 51/50
USPC ....................... 546/2, 10; 313/504
See application file for complete search history.

(56) References Cited

FOREIGN PATENT DOCUMENTS

| | | | |
|---|---|---|---|
| CN | 102329339 A | 1/2012 | |
| CN | 102496682 A | 6/2012 | |
| CN | 102648204 A | 8/2012 | |
| CN | 102718804 | * 10/2012 | .............. C07F 15/00 |
| CN | 102911214 A | 2/2013 | |
| WO | 2011/070990 A1 | 6/2011 | |

OTHER PUBLICATIONS

Cheng-Cheng Wang, et al; "Syntheses, Photoluminescence, and Electroluminescence of Iridium(III) Complexes with Fluorinated 2-Phenylpyridine as Main Ligands and Tertraphenylimidodiphosphinate as Ancillary Ligand", Eur. J. Inorg. Chem, pp. 5683-5693; First published Sep. 25, 2013.
Yong-Hui Zhou, et al; "Synthesis and Properties of Two Phosphorescence Iridium Complexes", Chinese Journal of Inorganic Chemistry 30(10):2288-2294; Oct. 2014.
First Chinese Office Action dated Nov. 17, 2016; Appln. No. 201510095127.0.
International Search Report and Written Opinion both dated Dec. 11, 2015; PCT/CN2015/083929.
Second Chinese Office Action dated May 19, 2017; Appln. No. 201510095127.0.

* cited by examiner

*Primary Examiner* — Charanjit Aulakh
(74) *Attorney, Agent, or Firm* — Ladas & Parry LLP

(57) ABSTRACT

A metal complex having a structural formula as follows, wherein, the metal atom M is selected from the group consisting of iridium (Ir), platinum (Pt), osmium (Os), rhenium (Re), ruthenium (Ru) and copper (Cu); $R_1$, $R_2$, $R_3$ and $R_4$ are independently selected from the group consisting of —F, —$CF_3$, —$CH_3$ and substituted phenyl; in the (C^N) substructure located on a left side of the metal atom M in the structural formula (I), C is located in a first aromatic or heteroaromatic ring, and N is located in a second heteroaromatic ring. The metal complex can be used in luminescent material of display devices.

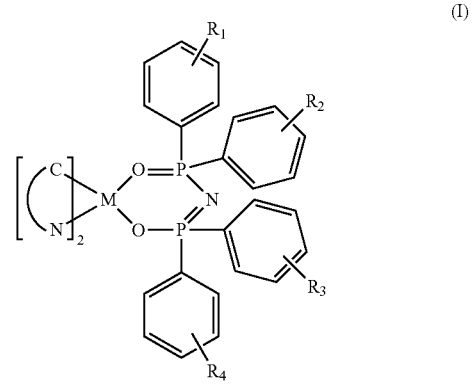

(I)

18 Claims, 3 Drawing Sheets

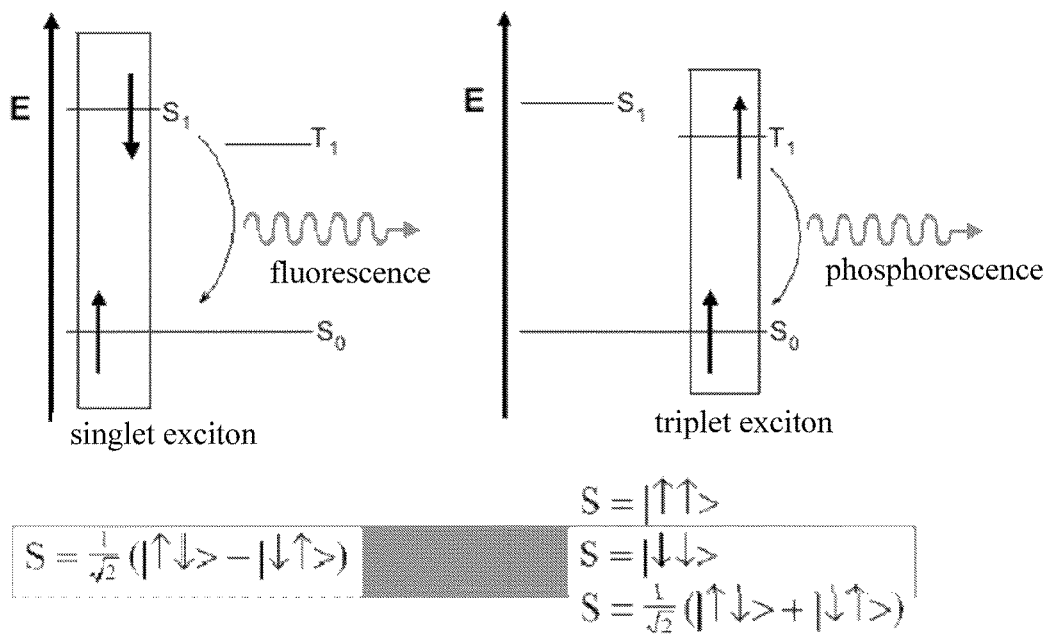

Fig.1

| dissolving a di-(substituted phenyl)phosphorus chloride having structural formula (II) and a di-(substituted phenyl)phosphorus chloride having structural formula (III) into anhydrous toluene and heating to reflux; adding hexamethyldisilazane (HMDS); and continuing to react under reflux after the addition has been completed, to obtain an intermediate product having structural formula (IV) | Step(1) |

| dissolving the intermediate product having structural formula (IV) into tetrahydrofuran (THF) to obtain a reaction solution; adding the mixed solution of hydrogen peroxide and THF into the reaction solution, and continuing to react after the addition has been completed, to obtain an auxiliary ligand having structural formula (V). | Step(2) |

| forming the main ligand having structural formula (VII) into a chloro-bridge compound having structural formula (VIII) by using MCl$_3$. | Step(3) |

| under an anhydrous oxygen-free condition, dissolving the chloro-bridge compound having structural formula (VIII) and a salification auxiliary ligand having structural formula (VI) into ethylene glycol monoethyl ether for reaction, to obtain the metal complex having structural formula (I); wherein the salification auxiliary ligand (VI) is obtained from the auxiliary ligand (V). | Step(4) |

Fig.2

METAL COMPLEX, PREPARATION METHOD AND USE THEREOF, AND DISPLAY DEVICE

TECHNICAL FIELD

The embodiments of the present invention relate to a metal complex, a preparation method and use thereof, and a display device using the metal complex as luminescent material.

BACKGROUND

Along with the booming development of the flat panel display technique, OLED (organic light-emitting diode) displays, in comparison with conventional liquid crystal displays (LCDs), not only are thinner and lighter, but also have many excellent properties, such as self-illumination, low power consumption, no back light requirement, no viewing angle restriction, high response speed, and etc., thus OLED displays have become the main trend of next generation of flat panel display technique and are used more and more widely.

The unique advantages of OLED devices have close relationships with the current carrier transfer materials, luminescent materials and electrode materials used in the devices, and the structures of the devices, wherein, luminescent material is a key part of the OLED device and can be divided into two types: fluorescent materials and phosphorescent materials. Fluorescent light is generated by electron transition between homogenous multiplets, and the maximum efficiency is only 25%. The low luminescence efficiency of fluorescent materials is caused by the limitation of the luminescence mechanism thereof.

SUMMARY

The embodiments of the present invention provide a metal complex, a preparation method and use thereof, and a display device using the metal complex as luminescent material.

The embodiments of the present invention employ the following technical solutions.

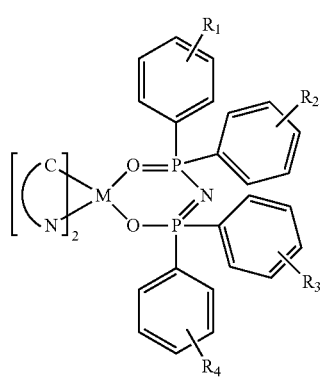

(I)

wherein, M is a metal atom selected from the group consisting of iridium (Ir), platinum (Pt), osmium (Os), rhenium (Re), ruthenium (Ru) and copper (Cu);

$R_1$, $R_2$, $R_3$ and $R_4$ are independently selected from the group consisting of —F, —$CF_3$, —$CH_3$ and substituted phenyl, such as phenyl substituted with —F, —$CF_3$ or —$CH_3$; and in the (C^N) substructure located on a left side of the metal atom M in the structural formula (I), C is located in a first aromatic or heteroaromatic ring, and N is located in a second heteroaromatic ring. In some embodiments, C, N and M are located in a third five-membered or six-membered heterocyclic ring. In some embodiments, the first aromatic or heteroaromatic ring, the second heteroaromatic ring and the third heterocyclic ring are different from each other. In some embodiments, the third heterocyclic ring is a five-membered or six-membered aromatic heterocyclic ring. In the present application, the term "a five-membered or six-membered aromatic heterocyclic ring" means a heterocyclic ring having five or six ring atoms in which at least one ring atom is not carbon atom, and at least one ring atom is located in an aromatic ring which is not the heterocyclic ring having five or six ring atoms.

In some embodiments, the metal atom M is iridium Ir.

In some embodiments, $R_1$, $R_2$, $R_3$ or $R_4$ is

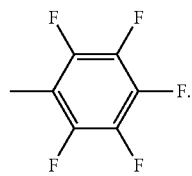

In some embodiments, $R_1$, $R_2$, $R_3$ and $R_4$ are para-substituted on respective benzene rings, that is, substituted at 4-position on respective benzene rings.

In some embodiments, $R_1$ and $R_3$ are the same and in the same substitution position on respective benzene rings; and $R_2$ and $R_4$ are the same and in the same substitution position on respective benzene rings.

In some embodiments, the (C^N) substructure is:

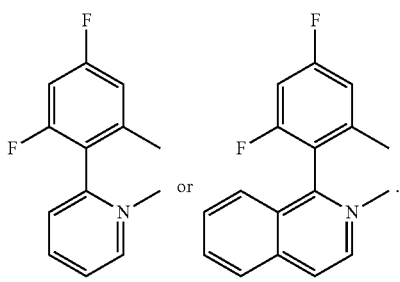

A preparation method of a metal complex, comprising:

(1) dissolving a di-(substituted phenyl)phosphorus chloride having structural formula (II) and a di-(substituted phenyl)phosphorus chloride having structural formula (III) into anhydrous toluene and heating to reflux, wherein, $R_1$, $R_2$, $R_3$ and $R_4$ are independently selected from the group consisting of —F, —$CF_3$, —$CH_3$ and substituted phenyl; adding hexamethyldisilazane (HMDS); and continuing to react under reflux after the addition has been completed, to obtain an intermediate product having structural formula (IV). In some embodiment, the hexamethyldisilazane (HMDS) is added dropwise.

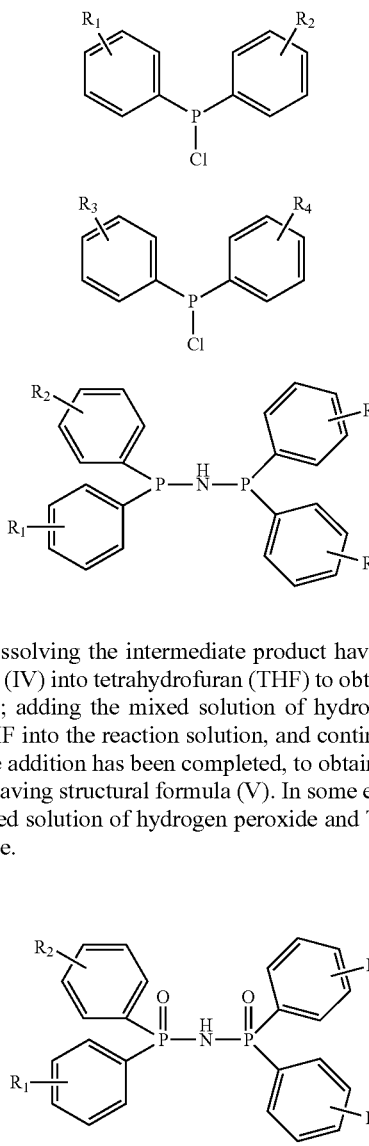

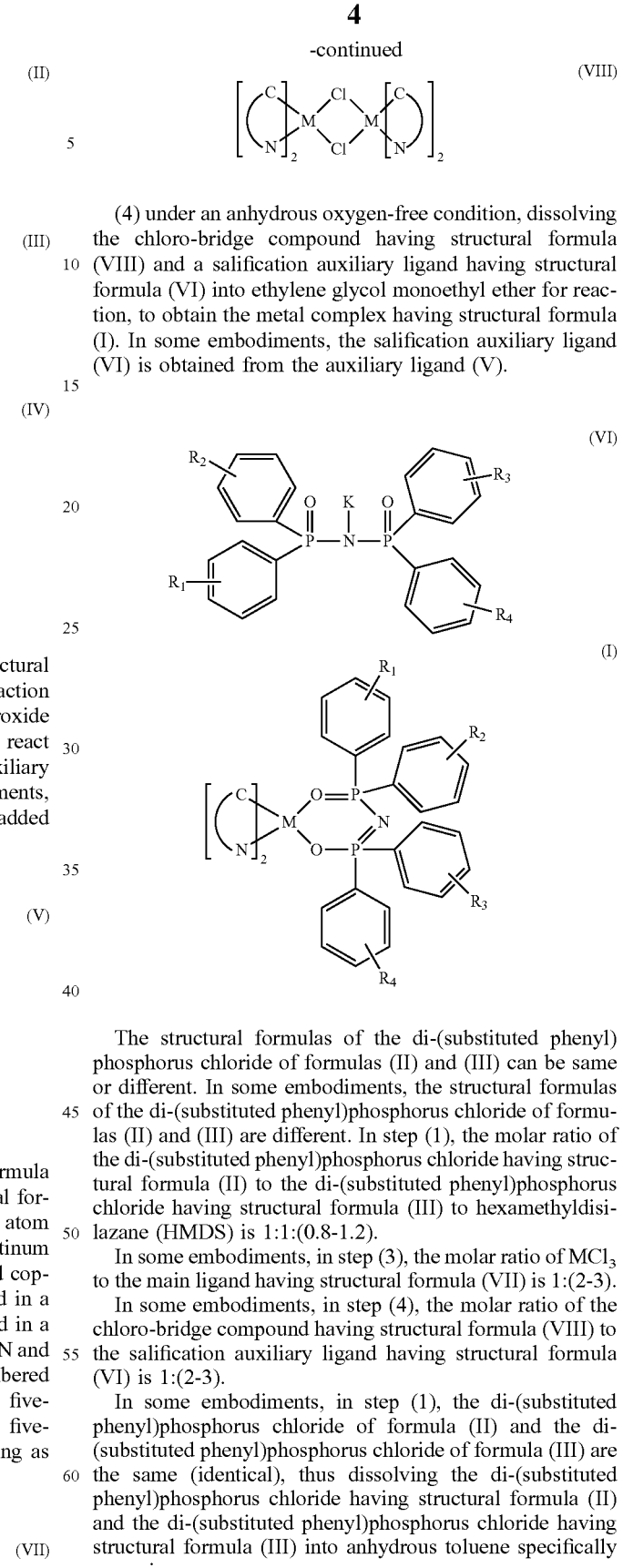

(2) dissolving the intermediate product having structural formula (IV) into tetrahydrofuran (THF) to obtain a reaction solution; adding the mixed solution of hydrogen peroxide and TI-IF into the reaction solution, and continuing to react after the addition has been completed, to obtain an auxiliary ligand having structural formula (V). In some embodiments, the mixed solution of hydrogen peroxide and THF is added dropwise.

(3) forming the main ligand having structural formula (VII) into a chloro-bridge compound having structural formula (VIII) by using $MCl_3$, wherein, M is a metal atom selected from the group consisting of iridium (Ir), platinum (Pt), osmium (Os), rhenium (Re), ruthenium (Ru) and copper (Cu); in the structural formula (VII), C is located in a first aromatic or heteroaromatic ring, and N is located in a second heteroaromatic ring. In some embodiments, C, N and M are located in a third five-membered or six-membered heterocyclic ring. In some embodiments, the third five-membered or six-membered heterocyclic ring is the five-membered or six-membered aromatic heterocyclic ring as defined in the present invention.

(4) under an anhydrous oxygen-free condition, dissolving the chloro-bridge compound having structural formula (VIII) and a salification auxiliary ligand having structural formula (VI) into ethylene glycol monoethyl ether for reaction, to obtain the metal complex having structural formula (I). In some embodiments, the salification auxiliary ligand (VI) is obtained from the auxiliary ligand (V).

The structural formulas of the di-(substituted phenyl) phosphorus chloride of formulas (II) and (III) can be same or different. In some embodiments, the structural formulas of the di-(substituted phenyl)phosphorus chloride of formulas (II) and (III) are different. In step (1), the molar ratio of the di-(substituted phenyl)phosphorus chloride having structural formula (II) to the di-(substituted phenyl)phosphorus chloride having structural formula (III) to hexamethyldisilazane (HMDS) is 1:1:(0.8-1.2).

In some embodiments, in step (3), the molar ratio of $MCl_3$ to the main ligand having structural formula (VII) is 1:(2-3).

In some embodiments, in step (4), the molar ratio of the chloro-bridge compound having structural formula (VIII) to the salification auxiliary ligand having structural formula (VI) is 1:(2-3).

In some embodiments, in step (1), the di-(substituted phenyl)phosphorus chloride of formula (II) and the di-(substituted phenyl)phosphorus chloride of formula (III) are the same (identical), thus dissolving the di-(substituted phenyl)phosphorus chloride having structural formula (II) and the di-(substituted phenyl)phosphorus chloride having structural formula (III) into anhydrous toluene specifically comprises:

dissolving the di-(substituted phenyl)phosphorus chloride having structural formula (II) into anhydrous toluene, the molar ratio of the di-(substituted phenyl)phosphorus chloride having structural formula (II) and hexamethyldisilazane (HMDS) being 2:(0.8-1.2). In the present application, anhydrous toluene means that the water content of the toluene is less than 300 ppm, such as less than 100 ppm, less than 50 ppm, or less than 10 ppm.

A use of the metal complex provided in the present invention as luminescent material in a display device is also disclosed.

A display device is also disclosed, in which the luminescent material contains the metal complex provided in the present invention.

In some embodiments, the display device is an OLED.

The metal complex provided in the present application has the structural formula (I). The metal atom M is selected from the group consisting of iridium (Ir), platinum (Pt), osmium (Os), rhenium (Re), ruthenium (Ru), copper (Cu) and other heavy metal atom, and the occurrence thereof may promote strong spin-orbit coupling. This strong spin-orbit coupling may achieve the radioactive decay of excited triplet state (the theoretical quantum efficiency can achieve 100%), which makes great progress over the electron transition between homogenous multiplets of fluorescent luminescent materials in the prior art (the theoretical quantum efficiency is only 25%). The introduction of strong polar O=P bond shortens the lifetime of excited state of the complex and improves the electron mobility of the material. The excellent electron transmission capability thereof can broaden the electron-hole recombination zones in the luminescent layer. Four benzene rings contribute to a larger molecular volume (bulk), and can decrease the interaction between molecules, thereby decreasing the triplet-triplet annihilation (TTA) and the efficiency roll-off phenomenon commonly in the preparation of luminescent devices. The metal complex of this structure has excellent luminescent performance when being used as luminescent material.

BRIEF DESCRIPTION OF THE DRAWINGS

In order to illustrate the technical solutions of the embodiments of the present invention more clearly, the figures of the embodiments are briefly described below. Apparently, the figures described below merely relate to some embodiments of the present invention rather than are limitative of the present invention.

FIG. 1 is schematic diagrams of the phosphorescence and fluorescence luminescent mechanisms.

FIG. 2 is a preparation method of the metal complex provided in an embodiment of the present invention.

REFERENCE SIGNS ON THE FIGURES

Figure 3:
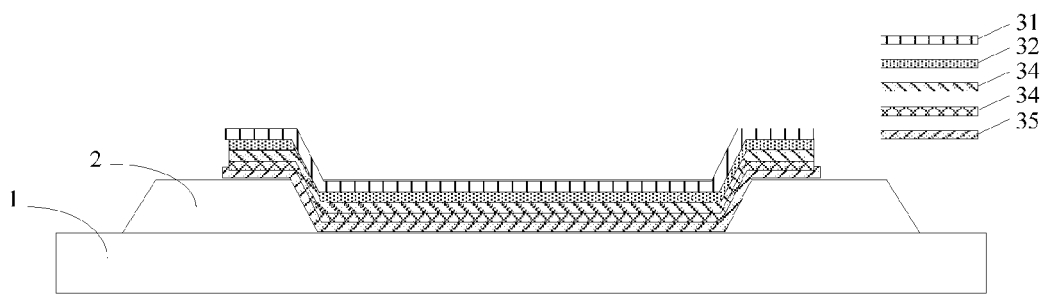
FIG. 3 is a simplified schematic diagram of the display device provided in an embodiment of the present invention.

1—substrate
2—simplified TFT (thin film transistor)
31—cathode buffer layer/electron injection layer
32—electron transport and hole barrier layer
33—pixel luminescent layer
34—hole transport material
35—ITO pixel electrode

DETAILED DESCRIPTION

To make the object, technical solutions, and advantages of the embodiments of the present invention clearer, the technical solutions of the embodiments of the present invention will be described below in a clearer and more complete way with reference to the figures of the embodiments of the present invention. Apparently, the embodiments described are only part, rather than all of the embodiments of the present invention. Based on the embodiments of the present invention described, all the other embodiments obtained by a person of ordinary skills in the art without paying inventive work fall into the scope of protection of the present invention.

The metal complex, the preparation method and the use thereof, and the display device provided in the embodiments of the present invention will be described below in details in combination of the figures.

The present invention provides a metal complex having the following structural formula:

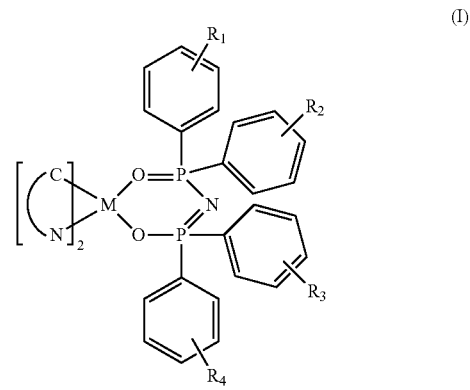

wherein, the metal atom M is selected from the group consisting of iridium (Ir), platinum (Pt), osmium (Os), rhenium (Re), ruthenium (Ru) and copper (Cu);

$R_2$, $R_3$ and $R_4$ are independently selected from the group consisting of —F, —$CF_3$, —$CH_3$ and substituted phenyl;

in the (C^N) substructure located on the left side of the metal atom M in the structural formula (I), C (carbon atom) is located in a first aromatic or heteroaromatic ring, and N (nitrogen atom) is located in a second heteroaromatic ring. In some embodiments, C, N and M are located in a third five-membered or six-membered heterocyclic ring. In some embodiments, the third five-membered or six-membered heterocyclic ring is an aromatic heterocyclic ring. In some embodiments, the first aromatic or heteroaromatic ring and the second heteroaromatic ring are fused or directly connected by a single bond.

The metal atom M is a heavy metal atom which, in the present application, means a metal atom of larger atomic number, such as a metal atom of an atomic number larger than or equivalent to 29. The high nuclear charge of the heavy metal atom induces or enhances the spin-orbital coupling effect which is proportional to the fourth power of the atomic number of the heavy metal atom. This strong spin-orbital coupling effect can achieve the radioactive decay of excited triplets.

From the viewpoints of the electron spin statistical theory, the generation probabilities of singlet excitons and three types of triplet excitons are the same, thus the generation probability of singlet excitons is only 25%, and the fluorescence luminescent material just utilizes the energy of this part of excited singlet state for illumination. Therefore the device prepared by using the fluorescence luminescent material has a theoretical maximum internal quantum efficiency of only 25%. Generally, the transition of electrons from the excited triplet state to the ground state (the singlet state) is forbidden and has a relative longer lifetime, and the transition is decayed usually in a non-radiation process. FIG. 1 briefly described the phosphorescence and fluorescence luminescent mechanisms.

In the phosphorescence luminescent mechanism, the occurrence of the heavy metal atoms in the luminescent complex may promote the strong spin-orbital coupling effect which is proportional to the fourth power of the atomic number of the heavy metal atom. This strong spin-orbital coupling effect can allow the radioactive decay of excited triplets, and the maximum internal quantum efficiency is increased to 100%. The occurrence of the heavy metal atoms makes the luminescent efficiency of phosphorescence complexes much greater than that of fluorescence complexes.

In the structural formula (I), the metal atom M forms a six-membered heterocyclic ring with O, P, N, P and O, wherein, the introduction of strong polar O═P bond shortens the lifetime of the excited state and improves the electron mobility of the material. The excellent electron transmission capability of the O═P bond can broaden the electron-hole recombination zones in the luminescent layer. It is needed to be noted that the position of the double bond on the heterocyclic ring is only schematic and the electrons on the double bond are shared by the whole heterocyclic ring.

Each of the two P atoms on the heterocyclic ring is connected with two substituted benzene rings. The introduction of the benzene rings forms a large-volume metal complex molecule which is beneficial to decreasing the interactive between molecules, thereby decreasing the triplet-triplet annihilation (TTA) and the efficiency roll-off phenomenon commonly in the preparation of luminescent devices.

In the structural formula (I), the (C^N) substructure located on the left side of the metal atom M plays a role of deciding the luminescent color when the complex is used as the luminescent material. The ligand providing the (C^N) substructure is referred to as the main ligand, while the ligand providing the structure on the right side of the metal atom M is referred to as the auxiliary ligand. Such as, the main ligand which can be used is selected from the compounds shown in the following structural formulas:

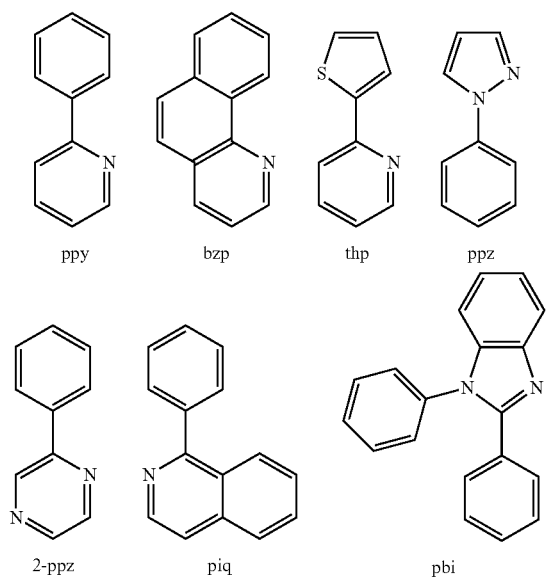

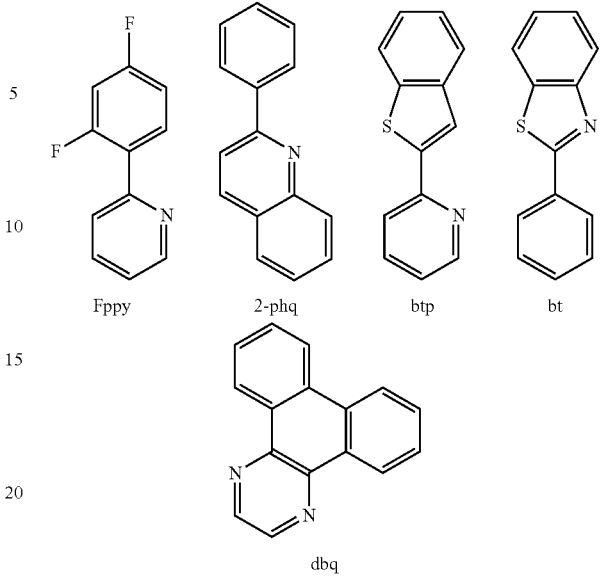

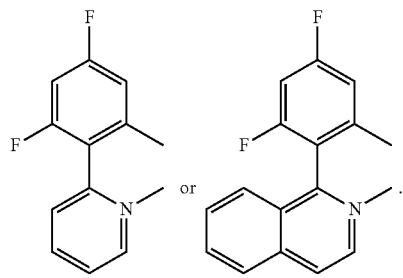

The corresponding (C^N) substructures can be easily obtained according to the above main ligand structures and are not described repeatedly herein.

In some specific embodiments, the (C^N) substructure is:

When the substructure is the former one, the metal complex is controlled to emit green light. When the substructure is the latter one, the metal complex is controlled to emit red light.

The metal complex provided in the embodiment of the present invention has the structural formula (I). The metal atom M is selected from the group consisting of iridium (Ir), platinum (Pt), osmium (Os), rhenium (Re), ruthenium (Ru), copper (Cu) and other heavy metal atom, and the occurrence thereof may promote strong spin-orbit coupling. This strong spin-orbit coupling may achieve the radioactive decay of excited triplet state (the theoretical quantum efficiency can achieve 100%), which makes great progress relative to the electron transition between homogenous multiplets of fluorescent luminescent materials in the prior art (the theoretical quantum efficiency is only 25%). The introduction of strong polar O═P bond shortens the lifetime of excited state of the complex and improves the electron mobility of the material. The excellent electron transmission capability thereof can broaden the electron-hole recombination zones in the luminescent layer. Four benzene rings contribute to a larger molecular volume, and can decrease the interaction between molecules, thereby decreasing the triplet-triplet annihilation (TTA) and the efficiency roll-off phenomenon commonly in the preparation of luminescent devices. The metal complex of this structure has excellent luminescent performance when being used as luminescent material.

In some embodiments, the metal atom M is iridium (Ir). When M is selected as Ir, the formed complex, in comparison with other heavy metal atoms, has a good thermal stability, a relative shorter lifetime of excited state and a high luminescence efficiency.

In some embodiments, the substituent group $R_1$, $R_2$, $R_3$ or $R_4$ on the four benzene rings of the structural formula (I) is pentafluorophenyl

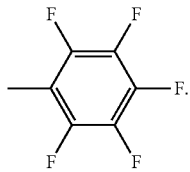

Pentafluorophenyl is a strong electron-donating group. When the four benzene ring of the structural formula (I) are substituted by this strong electron-donating group, the formed conjugated system can improve the charge transport performance of the molecule. In addition, the introduction of this group further increases the molecular volume, and decreases the interaction between molecules, thereby decreasing the triplet-triplet annihilation (TTA) and the efficiency roll-off phenomenon commonly in the preparation of luminescent devices.

In some embodiments, for further improving the electron-donating capability of the substituent groups on the benzene rings, $R_1$, $R_2$, $R_3$ and $R_4$ are para-substituted on respective benzene rings.

In some embodiments, for simplifying the molecular structure and simplifying the design and synthesis of the molecule, $R_1$ and $R_3$ are the same and have a same substitution position on respective benzene rings; and $R_2$ and $R_4$ are the same and have a same substitution position on respective benzene rings.

In some embodiments, both $R_1$ and $R_3$ are —$CF_3$ and are para-substituted on respective benzene rings. In some embodiments, both $R_2$ and $R_4$ are —$CH_3$ and are meta-substituted on respective benzene rings. In some embodiments, all of $R_1$, $R_2$, $R_3$ and $R_4$ are —$CH_3$ and are para-substituted on respective benzene rings. In some embodiments, all of $R_1$, $R_2$, $R_3$ and $R_4$ are pentafluorophenyl and are para-substituted on respective benzene rings, etc.

In correspondence with the above-mentioned metal complex, some embodiments of the present invention provide a preparation method of a metal complex. As shown in FIG. 2, the preparation method mainly comprises the following two steps, wherein, it is to be noted that the sequence of steps (1)-(2) and step (3) can be interchanged.

Step (1): dissolving the di-(substituted phenyl)phosphorus chloride having structural formula (II) and the di-(substituted phenyl)phosphorus chloride having structural formula (III) into anhydrous toluene and heating to reflux, wherein, $R_1$, $R_2$, $R_3$ and $R_4$ are independently selected from the group consisting of —F, —$CF_3$, —$CH_3$ and substituted phenyl; adding hexamethyldisilazane (HMDS); and continuing to react under reflux after the addition has been completed, to obtain an intermediate product having structural formula (IV). In some embodiment, the hexamethyldisilazane (HMDS) is added dropwise.

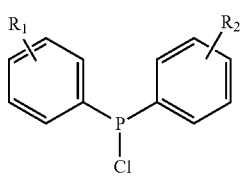

(II)

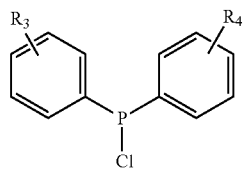

(III)

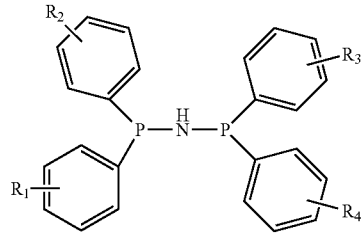

(IV)

The di-(substituted phenyl)phosphorus chloride of formula (II) and the di-(substituted phenyl)phosphorus chloride of formula (III) can have a same formula or different structural formulas. In some embodiments, the di-(substituted phenyl)phosphorus chloride of formulas (II) and the di-(substituted phenyl)phosphorus chloride of formula (III) have different formulas. In step (1), the molar ratio of the di-(substituted phenyl)phosphorus chloride having structural formula (II) and the di-(substituted phenyl)phosphorus chloride having structural formula (III) and hexamethyldisilazane (HMDS) is 1:1:(0.8-1.2).

In some embodiments, after adding HMDS, the reflux time is 5-7 hours, preferably 6 hours.

When the above di-(substituted phenyl)phosphorus chlorides are of different types, the reaction can be controlled poorly and the reaction is relatively complicated, therefore in order to simplifying the synthesis step and the molecular design and obtaining the target product to the greatest extent, the di-(substituted phenyl)phosphorus chloride having structural formula (II) and the di-(substituted phenyl)phosphorus chloride having structural formula (III) are preferably the same compound, thereby facilitating to obtain a high purity product, simplifying the subsequent separation, purification and other steps and increasing the productivity of the target product.

Step (2): dissolving the intermediate product having structural formula (IV) into tetrahydrofuran (THF) to obtain a reaction solution; adding the mixed solution of hydrogen peroxide and THF into the reaction solution, and continuing to react after the addition has been completed, to obtain an auxiliary ligand having structural formula (V). In some embodiments, the mixed solution of hydrogen peroxide and THF is added dropwise.

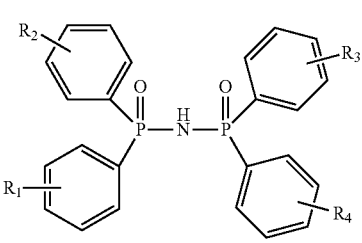

(V)

In some embodiments, in subsequent steps, a form of potassium salt of the auxiliary ligand (V) is commonly used. Therefore, in this step or before the step (4), the auxiliary ligand can be firstly formed into the potassium salt thereof. In some embodiments, the auxiliary ligand (V) is reacted with a base, such as but not limited to KOH or $K_2CO_3$. After that, diethyl ether is added to obtain a precipitate which is a salt, such as potassium salt, of the auxiliary ligand. In some embodiment, the concentration of the base, such as but not limited to KOH or $K_2CO_3$, is 2 wt %.

Step (3): forming the main ligand having structural formula (VII) into a chloro-bridge compound having structural formula (VIII) by using $MCl_3$, wherein, the metal atom M is selected from the group consisting of iridium (Ir), platinum (Pt), osmium (Os), rhenium (Re), ruthenium (Ru) and copper (Cu); in the structural formula (VII), C is located in a first aromatic or heteroaromatic ring, and N is located in a second heteroaromatic ring. In some embodiments, C, N and M are located in a third five-membered or six-membered heterocyclic ring. In some embodiments, the third five-membered or six-membered heterocyclic ring is an aromatic heterocyclic ring.

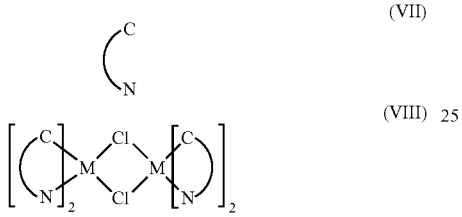

In some embodiments, in this step, under the anhydrous oxygen-free condition and under the protection of purging nitrogen gas, $MCl_3$ and the main ligand are dissolved into a mixed solvent of ethylene glycol monoethyl ether and water and refluxed, to obtain the chloro-bridge compound. In the present application, anhydrous oxygen-free means that no oxygen gas and water are intentionally added into the reaction system, such as the volume content of oxygen gas in the atmosphere is less than 0.01%, and the volume content of moisture (water) in the atmosphere is less than 0.01%.

In some embodiments, the ratio of ethylene glycol monoethyl ether to water is 3:(0.8-1.2), such as, the ratio thereof is 3:1.

In some embodiments, the reflux time is 18-22 hours, such as 20 hours.

Step (4): under the anhydrous oxygen-free condition, dissolving the chloro-bridge compound having structural formula (VIII) and a salification auxiliary ligand having structural formula (VI) into ethylene glycol monoethyl ether for reaction, to obtain the metal complex having structural formula (I), optionally the reaction temperature being 110-130° C., such as 130° C. or 120° C. The reaction time can be 22 to 26 hours, for example, 24 hours. In some embodiments, the salification auxiliary ligand (VI) is obtained from the auxiliary ligand (V)

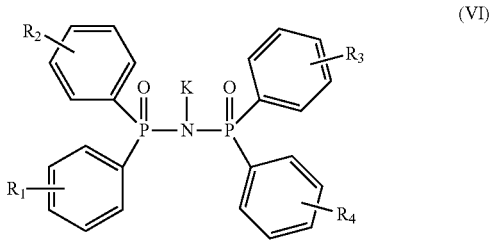

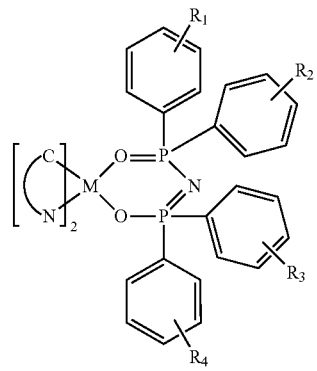

In some embodiments, the molar ratio of the chloro-bridge compound having structural formula (VIII) to the salification auxiliary ligand having structural formula (VI) is 1:(2-3).

In some embodiments, as described in step (2), the salification auxiliary ligand may be obtained by the reaction of the auxiliary ligand (V) and a base, such as but not limited to KOH or $K_2CO_3$.

In correspondence with the metal complex provided in the embodiment of the present invention, the present invention further provides a use of the metal complex as luminescent material in display devices. Because of the above mentioned excellent luminescence property of the metal complex, the metal complex can be suitably used as luminescent material in the display device. In some embodiments, it is used in an active matrix organic light-emitting diodes (AMOLEDs).

In correspondence with the metal complex provided in the embodiment of the present invention, the present invention further provides a display device, in which the luminescent material contains the metal complex provided in the present invention. In some embodiments, the luminescent material in the display device is the metal complex provided in the present invention. As shown in FIG. 3, 1 is a substrate; 2 is a simplified TFT; and 31 to 35 are successively: 31 cathode buffer layer/electron injection layer; 32 electron transport and hole barrier layer; 33 pixel luminescent layer; 34 hole transport material and 35 ITO (indium tin oxide) pixel electrode. In FIG. 3, the metal complex is used as luminescent material in the pixel luminescent layer 33. In FIG. 3, depending on the luminescent property of the metal complex used, the pixel luminescent layer may be a red light-emitting pixel luminescent layer, a green light-emitting pixel luminescent layer or a blue light-emitting pixel luminescent layer. In some embodiments, the display device may be an OLED display device.

Because the metal complex with the excellent luminescence property is used as the luminescent material thereof, the display has an excellent luminescence property and the efficiency roll-off phenomenon commonly in the existing luminescent devices is reduced.

To illustrate the metal complex and the preparation method thereof provided in the present invention better, the detailed embodiments are listed and described below.

Embodiment 1: Green Light-Emitting Ir Complex

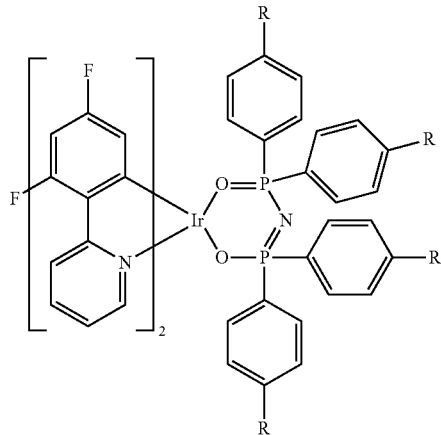

The synthesis steps thereof may be shown as the following series of reaction formulas:

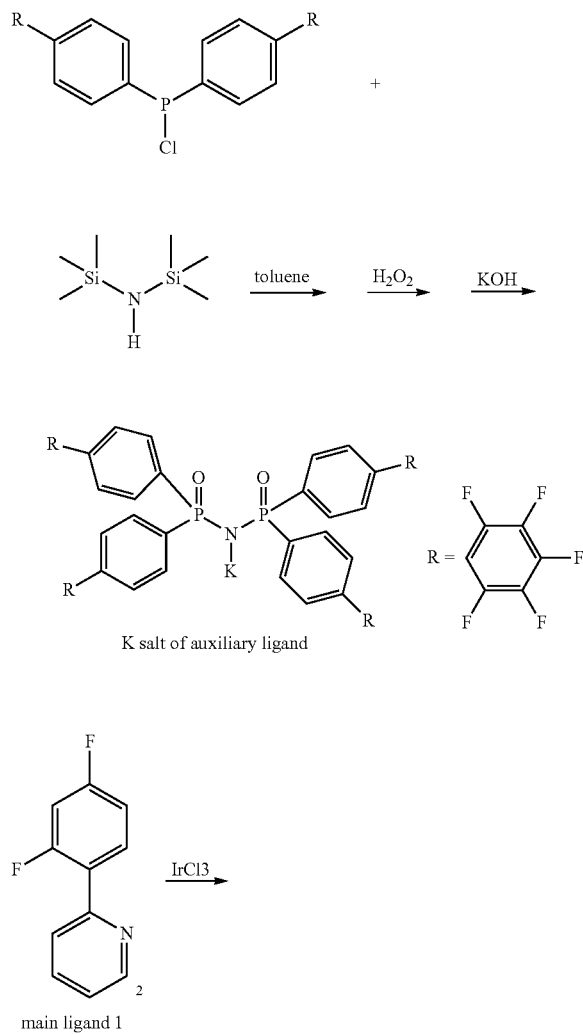

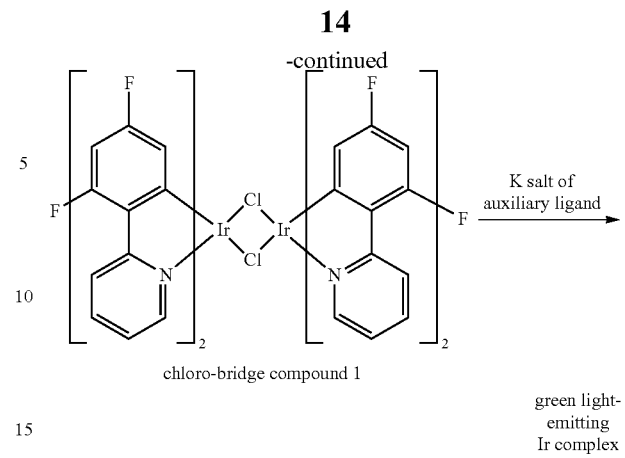

chloro-bridge compound 1

→ K salt of auxiliary ligand → green light-emitting Ir complex (1) The Synthesis of the Auxiliary Ligand and the Potassium Salt Thereof Under an anhydrous oxygen-free condition, 20 mmol di-(substituted phenyl) phosphorus chloride was dissolved in 30 mL anhydrous toluene and heated to reflux. 11 mmol hexamethyldisilazane (HMDS) was slowly added dropwise. After the addition had been completed, the reaction was continued for 6 hours under reflux. After the reaction was finished, the reaction was cooled and rotary evaporated to remove the reaction byproduct trimethylchlorosilane and toluene.

Then, the product was dissolved in 4 mL THF, and a mixed solution of 2 mL 30 wt % hydrogen peroxide and 10 mL THF was slowly added dropwise into the reaction liquid. After the addition had been completed, the reaction was carried out for 2 hours. After the reaction, the liquid was poured into 100 mL diethyl ether solution and a plenty of white-colored precipitates were formed. The precipitates were washed by using water and dried under vacuum, after which the product di-(di-(substituted phenyl)phospho)amide, i.e. the auxiliary ligand, was obtained.

At room temperature, 10 mL 2 wt % KOH solution in methanol was slowly added dropwise into the di-(di-(substituted phenyl)phospho)amide. After the addition had been completed, the reaction liquid was concentrated to 2 mL, then 20 mL diethyl ether was added. After vibrating and placing for a period of time, a plenty of white-colored precipitates were precipitated out, and then filtered and dried under vacuum, thereby obtaining white-colored solids, i.e. the potassium salt of the auxiliary ligand.

Productivity: 87%

Characterization of Chemical Properties:

$^1$H NMR (500 MHz, CDCl$_3$, ppm) δ 7.52 (dd, 8H), 8.00 (d, 4H), 11.20 (s, 1H)

MS(MALDI-TOF): m/z 1081 [M]$^1$

Element Analysis Results:

| | | | |
|---|---|---|---|
| Calculated values: | C (%): 53.30 | H (%): 1.58 | N (%): 1.30 |
| Measured values: | C (%): 53.00 | H (%): 1.62 | N (%): 1.35 |

(2) The Synthesis of the Metal Complex

The reaction was carried out under the anhydrous oxygen-free condition and under the protection of purging nitrogen gas. 4.58 mmol IrCl$_3$ and 11 mmol corresponding main ligand 1 were dissolved into 16 mL mixed solvent of ethylene glycol monoethyl ether and water with ethylene glycol monoethyl ether: water being 3:1, and refluxed for 20 hours, to form a dimer with a chlorine atom as the bond bridge, i.e. the chloro-bridge compound 1 (Ir bridge compound).

The reaction was carried out under the anhydrous oxygen-free condition. 0.20 mmol chloro-bridge compound 1 and 0.5 mmol potassium salt of the auxiliary ligand were dissolved in 10 mL ethylene glycol monoethyl ether, and reacted at 120° C. for 24 hours. After the reaction had been completed, a yellow-colored solid was obtained by column chromatography. After dried under vacuum and sublimated for purification, the green light-emitting Ir complex was obtained.

Productivity: 25%

Characterization of Chemical Properties:

$^1$H NMR (500 MHz, D$_6$-DMSO) δ=8.91 (d, J=5.2 Hz, 2H), 8.06 (d, J=8.4 Hz, 2H), 7.75 (t, J=7.8 Hz, 2H), 7.50-7.35 (m, 6H), 7.27-7.14 (m, 6H), 7.03 (td, J=7.7, 2.8 Hz, 4H), 6.93 (t, J=7.0 Hz, 2H), 6.69 (ddd, J=12.1, 9.5, 2.2 Hz, 2H), 5.38 (dd, J=8.9, 2.2 Hz, 2H) ppm. $^{31}$P NMR (500 MHz, D$_6$-DMSO) δ 23.28 (s) ppm. MADI-TOF, m/z: [M] calcd for C$_{70}$H$_{28}$F$_{24}$IrN$_3$O$_2$P$_2$, 1653[M]; found 1654.5[M+1]. Melting point: >310° C.

Element Analysis Results:

| Calculated values: | C (%): 50.86 | H (%): 1.71 | N (%): 2.54 |
| Measured values: | C (%): 50.82 | H (%): 1.65 | N (%): 2.50 |

Figure 4:
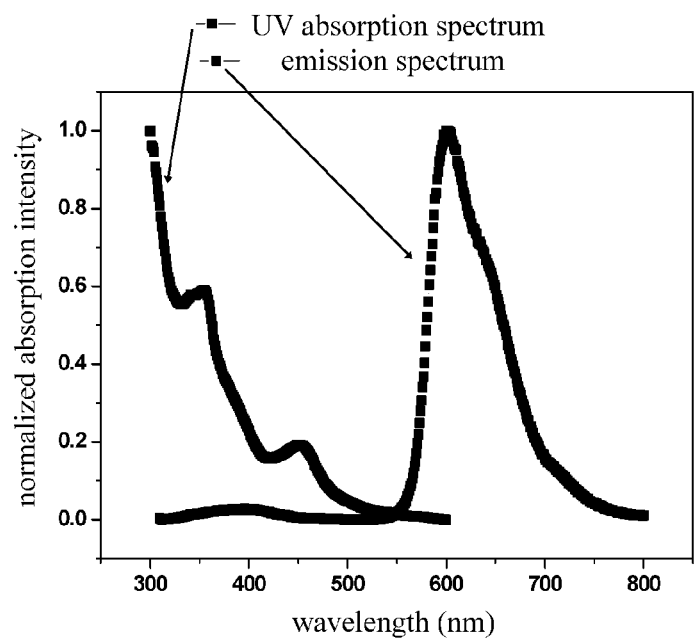
FIG. 4 is a UV absorption spectrum and emission spectrum of a green-emitting metal Ir complex in a methylene dichloride solution.

FIG. 4 provides the UV absorption spectrum and emission spectrum of the green light-emitting metal Ir complex in a methylene dichloride solution, wherein, the left-side decline curve is the UV absorption spectrum, and the right-side curve is the emission spectrum.

Embodiment 2: Red Light-Emitting Ir Complex

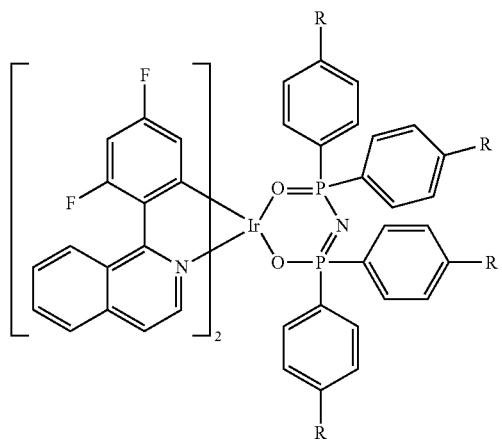

The synthesis steps may be shown as the following series of reaction formulas:

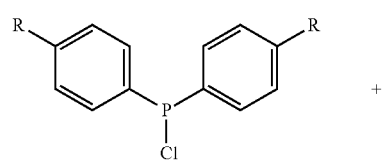

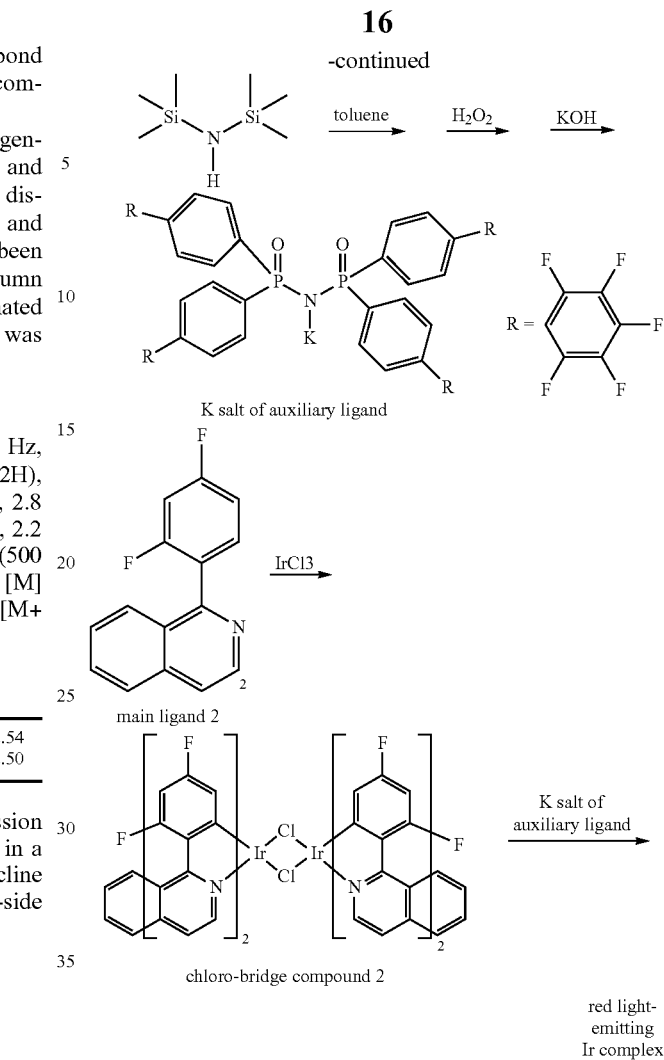

(1) The Synthesis of the Auxiliary Ligand and the Potassium Salt Thereof

The synthesis steps of the auxiliary ligand and the potassium salt thereof are the same as those in embodiment 1.

(2) The Synthesis of the Metal Complex

The synthesis steps of the metal complex are the same as those in embodiment

Productivity: 23%

Characterization of Chemical Properties:

$^1$H NMR (500 MHz, CDCl$_3$, ppm) δ 8.97 (d, J=6.3 Hz, 2H), 8.46-8.36 (m, 2H), 7.79-7.62 (m, 12H), 7.40-7.30 (m, 6H), 7.19-7.09 (m, 4H), 7.04 (d, J=6.3 Hz, 2H), 6.45-6.38 (m, 2H), 5.78-5.71 (m, 2H). MADI-TOF, m/z: [M] calcd for C$_{78}$H$_{32}$F$_{24}$IrN$_3$O$_2$P$_2$, 1753 [M]; found 1754.7 [M+1]. Melting point: >310° C.

Element Analysis Results:

| Calculated values: | C (%): 53.43 | H (%): 1.84 | N (%): 2.40 |
| Measured values: | C (%): 53.38 | H (%): 1.82 | N (%): 2.44 |

Figure 5:
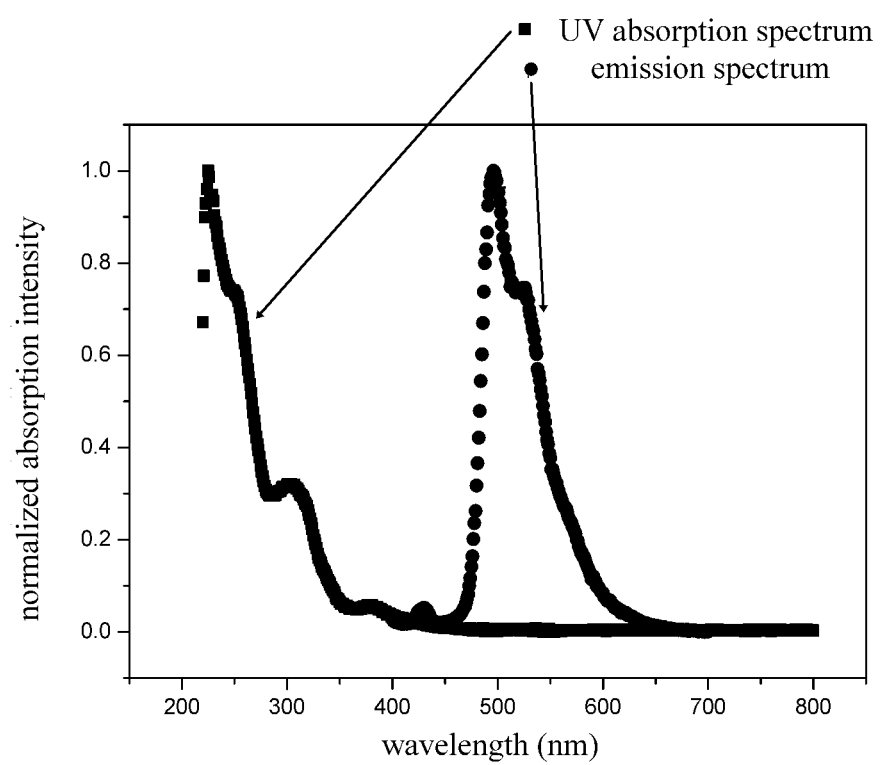
FIG. 5 is a UV absorption spectrum and emission spectrum of a red-emitting metal Ir complex in a methylene dichloride solution.

FIG. 5 provides the UV absorption spectrum and emission spectrum of the red light-emitting metal Ir complex in a methylene dichloride solution, wherein, the left-side decline curve is the UV absorption spectrum, and the right-side curve is the emission spectrum.

Embodiment 3: The Preparation of the Display Device

The conventional four-mask process was used to prepare TFT which specifically comprised a grid electrode, a grid insulation layer, an active layer, a source electrode, a drain electrode, an insulation layer and an ITO pixel electrode. A simplified TFT is shown in FIG. 2.

After being bombarded for 20 minutes, the substrate was vapor deposited with an organic layer. Firstly, 30 nm hole transport material TAPC was deposited on the ITO glass substrate, and then a luminescent layer of 15 nm was formed by coevaporating an object material and a subject material mcp, wherein the metal complexes of Embodiments 1 and 2 were used as green-emitting and red-emitting materials respectively; an existing blue-emitting Ir complex was used as blue-emitting material; and the concentrates thereof in the subject material is about 8 mol %. The following was: 45 nm of electron transport and hole barrier layer TPBi; 1 nm of LiF cathode buffer layer/electron injection layer; and 100 nm cathode aluminum. The sectional view formed finally is as shown in FIG. 3, wherein the green-emitting and red-emitting Ir complexes were synthesized by using the method of the present application; TAPC, mcp, TPBi and the blue-emitting Ir complex were common compounds and are commercially available. All organic materials were purified by low-pressure gradient vacuum sublimation before vapor deposition. The structural formulas of TAP, Cmcp, TPBi and blue-emitting Ir complex were as follows.

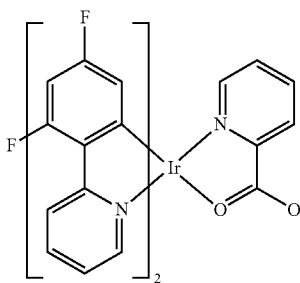

Blue Light-Emitting Ir Complex:

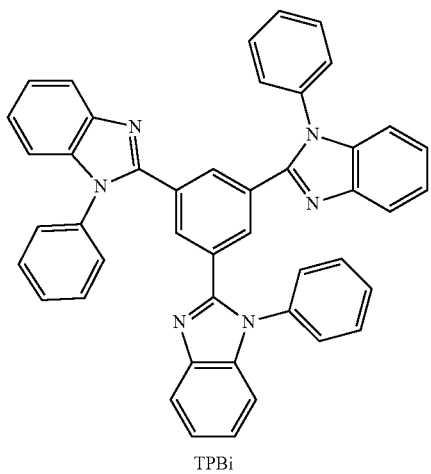

TPBi

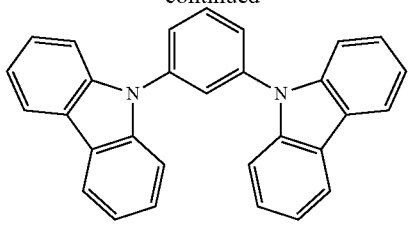

mep

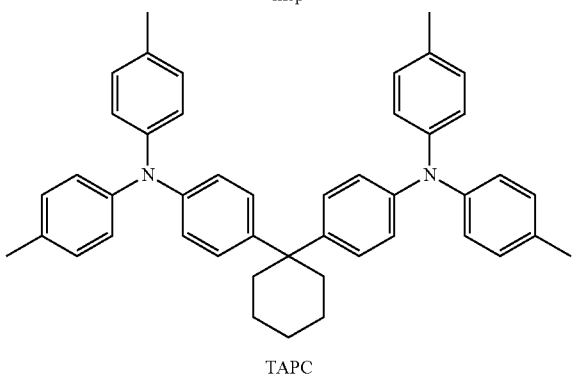

TAPC

The above description is merely exemplary embodiments which are not used for limiting the scope of protection of the present invention which is, however, determined by the attached claims.

The present application claims the priority of the Chinese Patent Application No. 201510095127.0 submitted on Mar. 3, 2015, and the content disclosed in the above Chinese patent application is incorporated by reference as part of this application.

What is claimed is:

1. A metal complex, having a structural formula (I):

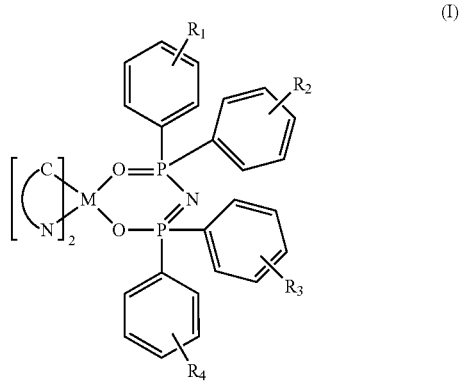

wherein, M is a metal atom selected from the group consisting of iridium (Ir), platinum (Pt), osmium (Os), rhenium (Re), ruthenium (Ru) and copper (Cu);

$R_1$, $R_2$, $R_3$ and $R_4$ are independently selected from the group consisting of —F, —$CF_3$, —$CH_3$ and substituted phenyl; and in the (C^N) substructure located on a left side of the metal atom M in the structural formula (I), C is located in a first six-membered aromatic or five-membered or six-membered heteroaromatic ring having zero or one heteroatom selected from nitrogen and sulfur, and N is located in a second five-membered or six-membered heteroaromatic ring having one or two heteroatom(s) selected from nitrogen and sulfur, wherein, at least one of $R_1$, $R_2$, $R_3$ or $R_4$ is

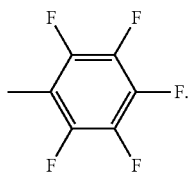

2. The metal complex as defined according to claim 1, wherein, C, N and M are located in a third five-membered or six-membered heterocyclic ring.

3. The metal complex as defined according to claim 1, wherein, $R_1$, $R_2$, $R_3$ and $R_4$ are para-substituted on respective benzene rings.

4. The metal complex as defined according to claim 1, wherein, $R_1$ and $R_3$ are identical and have a same substitution position on respective benzene rings; and $R_2$ and $R_4$ are identical and have a same substitution position on respective benzene rings.

5. The metal complex as defined according to claim 1, wherein, the (C^N) substructure is selected from the group consisting of:

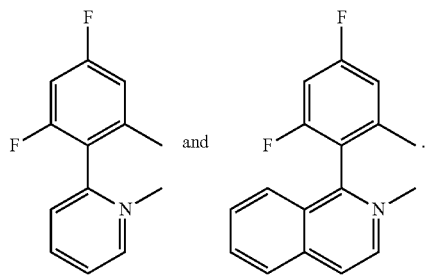

6. The metal complex as defined according to claim 1, wherein, the (C^N) substructure is derived from a material selected from the group consisting of following compounds which are substituted or unsubstituted:

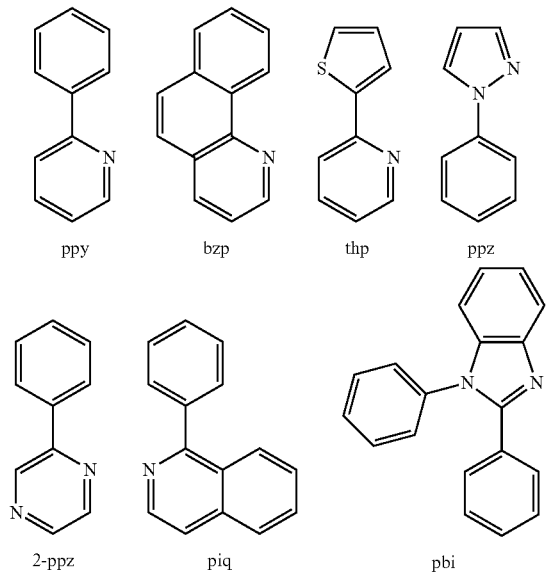

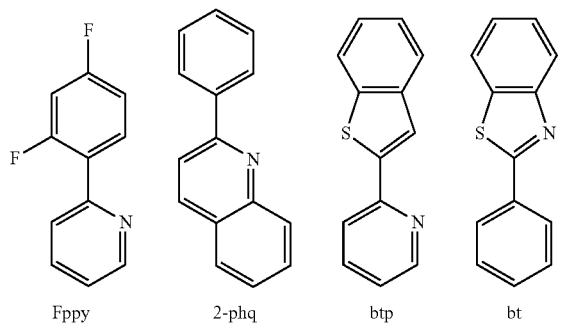

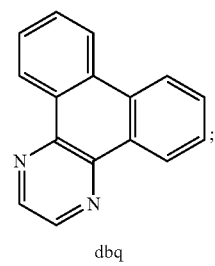

and wherein, in the case where the above compounds are substituted by a substituent group, the substituent group is selected from the group consisting of —F, —$CF_3$, —$CH_3$, and

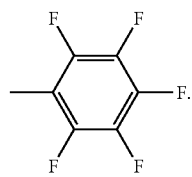

7. A preparation method of a metal complex, wherein, the preparation method comprises:

under an anhydrous oxygen-free condition, dissolving a chloro-bridge compound having structural formula (VIII) and a salification auxiliary ligand having structural formula (VI) into ethylene glycol monoethyl ether to react to obtain a metal complex having structural formula (I),

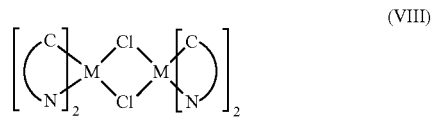

(VIII)

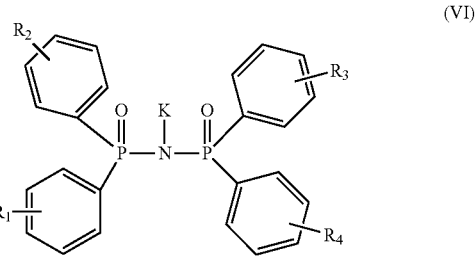

(VI)

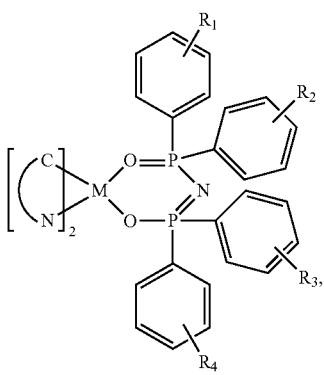

(I)

wherein, $R_1$, $R_2$, $R_3$ and $R_4$ are independently selected from the group consisting of —F, —$CF_3$, —$CH_3$ and substituted phenyl; metal atom M is selected from the group consisting of iridium (Ir), platinum (Pt), osmium (Os), rhenium (Re), ruthenium (Ru) and copper (Cu); and in the (C^N) substructure, C is located in a first six-membered aromatic or five-membered or six-membered heteroaromatic ring having zero or one heteroatom selected from nitrogen and sulfur, and N is located in a second five-membered or six-membered heteroaromatic ring having one or two heteroatom(s) selected from nitrogen and sulfur, wherein, at least one of $R_1$, $R_2$, $R_3$ or $R_4$ is

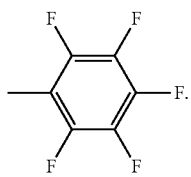

8. The method as defined according to claim 7, wherein, the salification auxiliary ligand (VI) is obtained from an auxiliary ligand having structural formula (V),

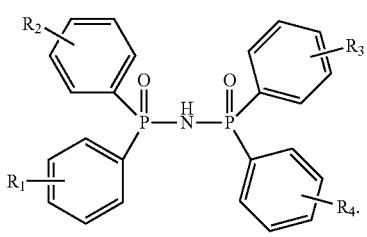

(V)

9. The method as defined according to claim 8, wherein, the auxiliary ligand (V) is prepared as follows:

dissolving a compound having structural formula (IV) into tetrahydrofuran (THF) to obtain a reaction solution; adding a mixed solution of hydrogen peroxide and THF into the reaction solution, and continuing to react after the addition has been completed, to obtain the auxiliary ligand having structural formula (V),

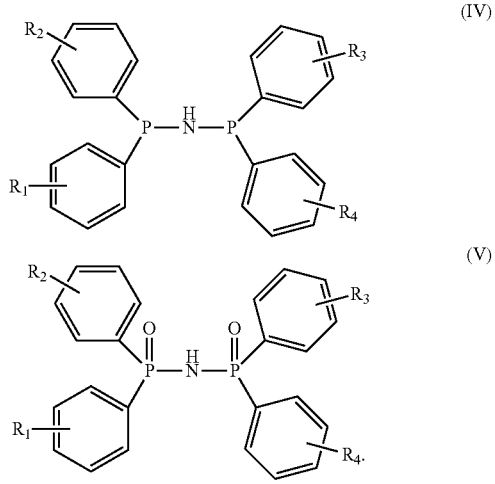

(IV)

(V)

10. The method as defined according to claim 7, wherein, the chloro-bridge compound having structural formula (VIII) is prepared as follows:

forming a main ligand having structural formula (VII) into the chloro-bridge compound having structural formula (VIII) by using $MCl_3$; in the structural formula (VII), C is located in a first aromatic or heteroaromatic ring, and N is located in a second heteroaromatic ring,

(VII)

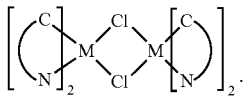

(VIII)

11. The method as defined according to claim 7, wherein, in the structural formula (I), C, N and M are located in a third five-membered or six-membered heterocyclic ring.

12. The method as defined according to claim 9, wherein, the compound having structural formula (IV) is prepared as follows:

dissolving a di-(substituted phenyl)phosphorus chloride having structural formula (II) and a di-(substituted phenyl)phosphorus chloride having structural formula (III) into anhydrous toluene and heating to reflux; adding hexamethyldisilazane (HMDS); and continuing to react under reflux after the addition has been completed, to obtain an intermediate product having structural formula (IV),

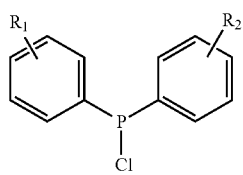

(II)

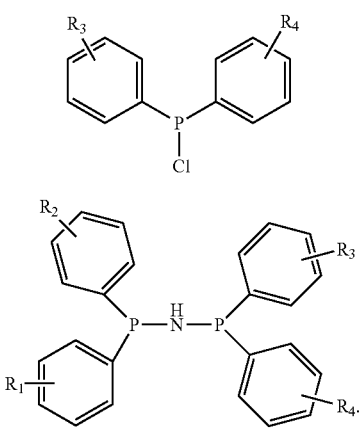

13. The preparation method of the metal complex as defined according to claim 12, wherein,
the di-(substituted phenyl)phosphorus chloride having formula (II) and the di-(substituted phenyl)phosphorus chloride having formula (III) are different; a molar ratio of the di-(substituted phenyl)phosphorus chloride having structural formula (II) to the di-(substituted phenyl) phosphorus chloride having structural formula (III) to hexamethyldisilazane (HMDS) is 1:1:(0.8-1.2).

14. The method as defined according to claim 10, wherein, a molar ratio of $MCl_3$ to the main ligand having structural formula (VII) is 1:(2-3).

15. The method as defined according to claim 7, wherein, a molar ratio of the chloro-bridge compound having structural formula (VIII) to the salification auxiliary ligand having structural formula (VI) is 1:(2-3).

16. The preparation method of the metal complex as defined according to claim 12, wherein,
the di-(substituted phenyl)phosphorus chloride of formula (II) and the di-(substituted phenyl)phosphorus chloride having structural formula (III) are identical; and dissolving the di-(substituted phenyl)phosphorus chloride having structural formula (II) and the di-(substituted phenyl)phosphorus chloride having structural formula (III) into anhydrous toluene specifically comprises:
dissolving the di-(substituted phenyl)phosphorus chloride having structural formula (II) into anhydrous toluene, the molar ratio of the di-(substituted phenyl)phosphorus chloride having structural formula (II) and hexamethyldisilazane (HMDS) being 2:(0.8-1.2).

17. A display device, wherein, a luminescent material of the display device contains the metal complex as defined according to claim 1.

18. The display device as defined according to claim 17, wherein, the display device is an organic light-emitting diode.

* * * * *